United States Patent [19]
Meister et al.

[11] Patent Number: 6,010,725
[45] Date of Patent: Jan. 4, 2000

[54] SPRAY-DRYING PROCESS

[75] Inventors: Niklaus Meister, Grosshoechstetten; Jürg Aebischer, Liebefeld; Martin Vikas, Konolfingen; Kurt Eyer, Thun; David De Pasquale, Konoflingen, all of Switzerland

[73] Assignee: Nestec S.A., Vevey, Switzerland

[21] Appl. No.: 08/877,801

[22] Filed: Jun. 18, 1997

[30] Foreign Application Priority Data

Jul. 9, 1996 [EP] European Pat. Off. .............. 96201922
Sep. 10, 1996 [EP] European Pat. Off. .............. 96202518

[51] Int. Cl.[7] .............................. A23C 1/04; A23L 3/46; A23L 3/3463
[52] U.S. Cl. .............................. 426/61; 426/471
[58] Field of Search .............................. 426/61, 531, 389, 426/402, 403, 407, 443, 465, 471

[56] References Cited

U.S. PATENT DOCUMENTS

| | | | |
|---|---|---|---|
| 3,065,076 | 11/1962 | Wenner et al. | 99/56 |
| 3,897,307 | 7/1975 | Porubcan et al. | 195/59 |
| 3,985,901 | 10/1976 | Barberan | 426/43 |
| 3,988,440 | 10/1976 | Bogdanov | 424/115 |
| 4,332,790 | 6/1982 | Sozzi et al. | 424/38 |
| 4,702,799 | 10/1987 | Tout | 159/48.1 |
| 5,296,221 | 3/1994 | Mitsuoka et al. | 424/93 J |
| 5,574,746 | 11/1996 | Ammon et al. | 373/9 |
| 5,591,428 | 1/1997 | Bengmark et al. | 424/93.45 |

FOREIGN PATENT DOCUMENTS

| | | |
|---|---|---|
| 0 063 438 A1 | 10/1982 | European Pat. Off. . |
| 0 199 535 | 10/1986 | European Pat. Off. . |
| 0 298 605 A1 | 1/1989 | European Pat. Off. . |
| 0 577 904 A1 | 1/1994 | European Pat. Off. . |
| 0 633 441 A1 | 7/1995 | European Pat. Off. . |
| 65390 | 10/1995 | Ireland . |
| 48-8830 | 3/1973 | Japan . |
| 57-45443 | 3/1982 | Japan . |
| 2-86766 | 3/1990 | Japan . |
| 2-86767 | 3/1990 | Japan . |
| 2-86768 | 3/1990 | Japan . |
| 2-86769 | 3/1990 | Japan . |
| 2-86770 | 3/1990 | Japan . |
| 7-308830 | 11/1995 | Japan . |
| 7413373 | 10/1974 | Netherlands . |
| 724113 | 3/1980 | U.S.S.R. . |
| 1097253 | 6/1984 | U.S.S.R. . |
| 1227145 | 4/1986 | U.S.S.R. . |
| 1292706 | 2/1987 | U.S.S.R. . |
| 1581257 | 7/1990 | U.S.S.R. . |

OTHER PUBLICATIONS

A. Chopin et al., "Destruction de *Microbacterium lacticum, Escherichia coli* et *Staphylococcus aureus* au cours du séchage du lait par atomisation. II. Influence des conditions de séchage", *Can. J. Microbiol.*, vol. 23, No. 6 (1977) pp. 755–762.

T. Fujisawa et al., Taxonomic Study of the *Lactobacillus acidophilus* Group, with Recognition of *Lactobacillus gallinarum* sp. nov. and *Lactobacillus johnsonii* sp. nov. and Synonymy of *Lactobacillus acidophilus* Group A3 (Johnson et al. 1980) with the Type Strain of *Lactobacillus amylovorus* (Nakamura 1981), *Int. J. Syst. Bacteriol.*, vol. 42, No. 3 (1992) pp. 487–491.

J. Jensen, "Agglomerating, Insatantizing, and Spray Drying", *Food Technology* (Jun. 1975) pp. 60–71.

E.J. Schiffrin et al., "Immunomodulation of Human Blood Cells Following the Ingestion of Lactic Acid Bacteria", *J. Dairy Sci.*, vol. 78, No. 3 (1995) pp. 491–497.

Official Journal of the European Communities, No. OJ L49/12 (1996).

Derwent WPI Acc No: 80–87725C/198049, English language abstract of SU 724113A, 1980.

Derwent WPI Acc No: 86–318102/198648, English language abstract of SU 1227145A, 1986.

Derwent WPI Acc No: 87–319054/198745, English language abstract of SU 1292706A, 1987.

Derwent WPI Acc No: 90–137109/199018, English language abstract of JP 2086766A, 1990.

Derwent WPI Acc No: 90–137110/199018, English language abstract of JP 2086767A, 1990.

Derwent WPI Acc No: 90–137111/199018, English language abstract of JP 2086768A, 1990.

Derwent WPI Acc No: 90–137112/199018, English language abstract of JP 2086769 A, 1990.

Derwent WPI Acc No: 90–137113/199018, English language abstract of JP 2086770 A, 1990.

Derwent WPI Acc No: 91–176233/199124, English language abstract of SU 1581257A, 1991.

Derwent WPI Acc No; 96–022582/199603, English language abstract of IE 65390B, 1996.

Derwent WPI Acc No: 96–044526/199605, English language abstract of JP 7308830 A, 1996.

*Primary Examiner*—Keith Hendricks
*Attorney, Agent, or Firm*—Pennie & Edmonds LLP

[57] ABSTRACT

Spray-drying process in which a composition of microorganisms beneficial for human health is prepared and then reduced to a powder by spraying in a spray-drying device having a heated air inlet temperature of 200–400° C. and an air outlet temperature of 40–90° C., the residence time of the composition in the device being adjusted so as to obtain at least 1% survival of the microorganisms after drying.

14 Claims, No Drawings

SPRAY-DRYING PROCESS

TECHNICAL FIELD

The subject of the invention is a new process for spray-drying a composition that contains microorganisms.

BACKGROUND ART

To dry microorganisms, industry needs to have processes which are easy to use and which are economical. Spray-drying generally consists in spraying, in a chamber, a suspension of microorganisms in a stream of hot air, the chamber comprising, for this purpose, an inlet for heated air, an outlet for discharging air and an outlet for recovering the powder of dried microorganisms.

The spray-drying of microorganisms has, however the disadvantage of damaging, or even killing the microorganisms as the drying temperature becomes too high.

U.S. Pat. No. 3,985,901 (Instituto de Biologia Aplicada) explains, indeed, that a temperature of 180° C. to 300° C., at the inlet of a spraying device, is capable of killing all the live organisms. These observations are also confirmed in EP298605 (Unilever: page 2, lines 43–48), and EP63438 (Scottish Milk Marke: page 1, lines 14–21).

Some species of lactic acid bacteria are, however, naturally heat-resistant, that is to say they are capable of withstanding relatively high temperatures. Chopin et al. have thus shown that it is possible to spray-dry, at 215° C., a sporulating culture of *Microbacterium lacticum* and to obtain slightly more than 10% survival after drying (Canadian J. Microb., 23, 755–762, 1977). Unfortunately, these species generally form part of the contaminating flora in foods which is responsible for the appearance of bad taste. These heat-resistant lactic acid bacteria are therefore not suitable for human consumption ("Fundamentals of Food Microbiology", Marion L. Fields, AVI Publishing Comp, Westport, 1979).

In conclusion, the spray-drying temperature is thus one of the factors limiting the viability of the microorganisms traditionally used in the fermentation of food products. It can in fact be noted that all the conventional processes for spray-drying microorganisms use in practice a heated air inlet temperature of the order of 100–180° C., and thus reach temperatures where microorganisms are damaged or killed. Furthermore, these processes also resort to the use of protective agents to keep the dried microorganisms alive.

NL7,413,373 (DSO Pharmachim) describes a process for spray-drying cereals fermented by lactic acid bacteria in which the air inlet and outlet temperatures are 150° C. and 75° C. respectively.

J73008830 (Tokyo Yakult Seizo) describes a process for spray-drying microorganisms in which an air inlet temperature on the order of 120–155° C., an air outlet temperature on the order of 40–55° C. and protective chemical agents are used.

J57047443 (Minami Nippon Rakun) describes a similar drying process where the air inlet and outlet temperatures are on the order of 105–150° C. and 55–70° C. respectively.

J02086766, J02086767, J02086768, J02086769 and J02086770 (all "Kubota") describe processes for spray-drying microorganisms in which the air inlet and outlet temperatures are on the order of 110–180° C. and 70–75° C. respectively.

Finally, SU724113 (Kiev Bacterial Prep.), SU1097253 (Protsishin et al.), SU1227145 (Protsishin et al.), SU1292706 (Appl. Biochem. Res.) and SU1581257 (Dairyland Food Labs.) describe processes for spray-drying a bacterial culture in which the air inlet and outlet temperatures are on the order of 60–165° C. and 30–75° C. respectively.

It should be emphasized that limiting the drying temperature to less than 200° C., during spray-drying of microorganisms, limits the yield of the process correspondingly. The objective of the present invention is to overcome this disadvantage without killing all the microorganisms in the process.

SUMMARY OF THE INVENTION

To this effect, the present invention relates to a spray-drying process in which a composition comprising water and microorganisms beneficial for the human diet is prepared and is then reduced to a powder by spraying the composition in a spray-drying device having a heated air inlet temperature of 200–400° C. and an air outlet temperature of 40–90° C. to provide a dry powder, with the residence time of the composition in the device being controlled or adjusted so as to obtain survival of at least 1% to 10% or more of the microorganisms after drying.

It has been found surprisingly that a spray-drying device having an air inlet temperature greater than 200° C., and even greater than 300° C., does not damage or causes little damage to the microorganisms which are beneficial for the human diet, as long as the residence time of the droplets in the device is sufficiently short so that the internal temperature of the cells does not become lethal. It has indeed been observed that the internal temperature of the sprayed droplets cannot exceed about 40–70° C. because of cooling caused by the evaporation of water. The invention thus consists in the selection of the operating conditions so that the sprayed droplets arrive in a dry form only at the outlet of the drying device.

It has been observed that a very rapid drying of the microorganisms promotes good survival. The use of high air inlet temperatures can thus lead to practically instant drying.

It has also been observed that excellent survival of the microorganisms is obtained when a culture of microorganisms and a food composition are sprayed together.

DETAILED DESCRIPTION OF THE PREFERRED EMBODIMENTS

To carry out the present process, a culture of a microorganism, which may be a bacterium, a yeast, a fungus or a mixture of these microorganisms, is prepared. A person of ordinary skill in the art is capable of selecting the culture medium which is most suitable for the growth of the microorganisms.

Preferably, there is prepared a culture of at least one microorganism chosen from the group formed by lactic acid bacteria beneficial for human health, especially bifidobacteria such *Bifidobacterium infantis,* lactococci such as *Lactococcus lactis* subsp. *lactis, Lactococcus lactis* subsp. *cremoris, Lactococcus lactis* subsp. *lactic biovar diacetylactis,* streptococci such as *Streptococcus thermophilus, Streptococcus faecalis, lactobacilli* such as *Lactobacillus delbrueckii* subsp. *bulgaricus, Lactobacillus acidophilus* (comprising 6 subgroups including *L. johnsonii;* see Fujisawa et al., Int. J. Syst. Bact., 42, 487–491, 1992), *Lactobacillus helveticus, Lactobacillus farciminis, Lactobacillus alimentarius, Lactobacillus casei* subsp. *casei, Lactobacillus delbruckii* subsp. *lactis, Lactobacillus sake, Lactobacillus curvatus,* pediococci such as *Pediococcus*

*pentosaceus, Pediococcus acidilactici, Pediococcus halophilus*, staphylococci such as *Staphylococcus xylosus, Staphylococcus carnosus*, micrococci such as *Micrococcus varians;* yeasts especially of the genus Debaromyces, Candida, Pichia, Torulopsis and Saccharomyces such as *Debaromyces hansenii, Candida krusei, Pichia saitoi, Torulopsis holmii, Torulopsis versatilis, Torulopsis etchellsii, Saccharomyces cerevisiae* for example *S. cerevisiae* NCIMB 40612 described in EP663441, *Saccharomyces rouxii;* and fungi especially of the genus Aspergillus, Rhizopus, Mucor and Penicillium such as *Aspergillus oryzae, Aspergillus phoenicis, Aspergillus niger, Aspergillus awamori, Rhizopus oryzae, Rhizopus oligosporus, Rhizopus japonicus, Rhizopus formosaensis, Mucor circinelloides, Mucor japanicus, Penicillium glaucum* and *Penicillium fuscum*.

The invention is particularly appropriate for microorganisms which are sensitive to spray-drying conditions, especially those which are sensitive to heat (heat-sensitive) and/or to the presence of air (preferential anaerobes). Among the microorganisms which are particularly sensitive, there may be included the probiotic lactic acid bacteria. Within the framework of the present invention, probiotic bacteria are defined as lactic acid bacteria which are capable of adhering to human intestinal cells, of excluding pathogenic bacteria on human intestinal cells and of acting on the human immune system by allowing it to react more strongly to external aggression, for example by increasing the phagocytosis capacities of the granulocytes derived from human blood (J. of Dairy Science, 78, 491–197, 1995).

By way of example, there may be used the strain *Lactobacillus acidophilus* CNCM I-1225 described in EP577904. This strain was recently reclassified among *Lactobacillus johnsonii*, following the new taxonomy proposed by Fujisawa et al. which is now the reference with regard to the taxonomy of acidophilic lactobacilli (Int. J. Syst. Bact., 42, 487–791, 1992). Other probiotic bacteria are also available, such as those described in EP199535 (Gorbach et al.), U.S. Pat. No. 5,591,428 (Bengmark et al.) or in U.S. Pat. No. 5,296,221 (Mitsuoka et al.).

This culture of microorganisms may comprise, before or after fermentation, at least one protective chemical agent known to enhance the survival of the microorganisms during drying and/or during the preservation of the powder. Persons skilled in the art have abundant literature on these protective agents. To this effect, the protective agents described in patents U.S. Pat. No. 3,897,307, U.S. Pat. No. 4,332,790, J73008830, J57047443, J02086766, J02086767, J02086768, J02086769, J02086770, SU724113, SU1097253, SU1227145, SU1292706 and SU1581257 are useful in this invention and the contents of those patents are expressly incorporated by reference into the description of the present invention as necessary for the understanding of the invention. As a general guide, these protective agents typically are vitamins such as ascorbic acid, amino acids or their salts such as lysine, cysteine, glycine and sodium glutamate, proteins or protein hydrolysates which may be obtained from milk or soya, sugars such as lactose, trehalose, sucrose, dextrin and maltodextrin, and fats especially a butter fat (butter oil), palm, groundnut, cocoa, rapeseed or soya fat, for example. These protective agents may be added to the culture in an amount of about 0.1 to 80% by weight for example.

The culture of microorganisms preferably contains at least $10^7$ colonies of live cells per gram or cfu/g (cfu is the abbreviation for "colony forming unit"). It may also be chosen to concentrate this culture, for example by centrifugation, in order to increase the titer of live cells to at least $10^8$ cfu/g, and preferably to $10^8$–$10^{11}$ cfu/g.

If a powder consisting mainly of microorganisms is desired, the culture of microorganisms may be spray-dried directly. On the other hand, if a dehydrated food composition, easily dispersible in water and comprising such live microorganisms is desired, it is preferable to dry at the same time all the components of this composition rather than to prepare it by mixing the various constituents already in dry forms. The formation of lumps or of undesirable precipitates is thus avoided.

In a first embodiment for preparing a dehydrated food composition, the culture of microorganisms is thus mixed with a liquid food composition, where appropriate the mixture may be concentrated to a water content on the order of less than 70%, then the mixture may be spray-dried under the drying conditions according to the invention. This embodiment is particularly appropriate for milk-based dehydrated compositions comprising lactic acid bacteria which are not very sensitive to spray-drying, that is to say which are capable of surviving in an amount of at least about 10–50% under the drying conditions according to the invention. More particularly, a culture of microorganisms may thus be mixed with a food composition so as to obtain a mixture in which at least 80% by dry weight of the constituents is derived from the food composition, then the mixture can be spray-dried under the drying conditions according to the invention.

In a second embodiment for preparing a dehydrated food composition, a composition comprising the microorganisms and a food composition may also be reduced to a powder together in the spray-drying device. This embodiment is particularly appropriate for milk-based dehydrated compositions comprising lactic acid bacteria which are sensitive to spray-drying, that is to say which are incapable of surviving in an amount of at least about 10–50% under the drying conditions according to the invention. More particularly, it is possible to dry together, that is to say at the same time and in the same chamber, 1 part of a culture of microorganisms and at least 1 part and typically 1 to 1000 parts of a food composition, the parts being calculated in the dry state.

Preferably, the food composition which is used to prepare the dehydrated food composition is a liquid composition in which at least one of the components is chosen from the group formed by milk, meat, fish, a fruit and a vegetable. Preferably, the food composition is concentrated, before spraying it, to a water content of less than 70% by weight.

This food composition may thus comprise a cooked or raw finely divided part derived from an edible plant, whether it is a seed, a root, a tuber, a stem, a leaf, a flower or a fruit. Among the preferred plants, there may be distinguished more particularly leaves, especially leek, asparagus, fennel and cabbage; stems, especially rhubarb and broccoli; seeds such as cocoa, pea, soya or obtained from cereals; some roots, especially carrot, onion, radish, celery and beet; tubers, especially cassava and potato; and fruits, especially tomato, courgette, aubergine, banana, apple, apricot, melon, water melon, pear, plum, peach, cherry, kiwi, sea buckthorn berry, medlar and mirabelle cherry. It is also possible to use, as plants, mushrooms, especially *Agaricus bisporus, Pleurotus ostreatus, Boletus edulis* or *Lentinus edodes*, for example.

This food composition may also comprise a cooked or raw finely divided part derived from an animal, whether it is milk, egg, meat, fish and/or a fraction thereof, especially a protein fraction and/or a protein hydrolysate. This food composition may thus be a hydrolyzed and hypoallergenic cow's milk complying with the European Directive 96/4/EC (Official Journal of the European Communities, No OJ L49/12, 1996).

The spray-drying devices traditionally used for the industrial manufacture of a milk or coffee powder may be particularly well suited to the needs of the present invention (see Jensen J. D., Food Technology, June, 60–71, 1975). By way of example, it is possible to easily adapt either of the spray-drying devices described in IE65390 (Charleville Res. LTD) and U.S. Pat. No. 4,702,799 (Nestlé).

Preferably, these devices have, in operation, an area at very high temperature (200–400° C.) at the end of the spray nozzle, it being possible for the area to represent up to 50% of the volume of the chamber, and preferably about 0.1% to 20%, with the rest of the device having a lower temperature which may reach the air outlet temperature. The device described in U.S. Pat. No. 3,065,076 (Nestlé) particularly meets these needs.

Preferably, these devices also have, in operation, an additional air inlet, the additional air having a temperature chosen so as to adjust the temperature of the air at the outlet of the device. This additional air inlet is generally situated near the heated air inlet.

If it is desired to heat together a composition comprising microorganisms and another food composition, it is necessary to have at least one spray nozzle per composition. In operation, the position of the spray nozzles is not critical. It is thus possible to simultaneously spray the two compositions in the area at very high temperatures. It is also possible to spray the food composition in the area at a very high temperature, and at the same time to spray the microorganisms in an area having a lower temperature.

The invention also provides an appropriate selection of the residence time of the microorganisms in the drying device. Preferably, the sprayed droplets arrive in a dry form towards the outlet of the device, that is to say where the outlet temperature is about 40–90° C. This residence time may be adjusted with the aid of various parameters for regulating a spray-drying device, such as the pressure for spraying the droplets, the pressure of the hot air stream and/or the distance which the droplets have to cover in the drying chamber. It is not possible to provide herein precise values for each parameter involved in adjusting the residence time, since these parameters and their associated values depend on the type of spray-drying device used. As a guide, the pressure applied at the end of the nozzles for spraying the microorganisms or the food composition may be between about 5–250 bar, and the hot air pressure at the inlet of the device may be between about 100 and 200 mbar. Thus, to simplify the definition of this adjustment of the residence time of the culture according to the invention, it will be accepted that this time complies with the present invention if at least 1% of the bacteria which have just been dried survive, persons skilled in the art being indeed capable of selecting the appropriate operating parameters to achieve this result.

The rate of survival of the bacteria is based on the number of microorganisms that are in the liquid to be dired. The 1% survival during spray drying is considered to be totally acceptable, since the liquid mixture which is subjected to the spray dring conditions initially contains more than $10^8$ cfu/g. Thus, after drying, more than $10^6$ cfu/g are still active and alive.

Preferably, the residence time of the culture in the drying device is adjusted so as to also obtain a powder having a water activity (Aw) at 25° C. of between about 0.05 and 0.5. Indeed, the best survival rates after drying and during preservation are obtained for a powder having this water activity range.

Likewise, the best survival rates after drying and during preservation are obtained when the drying device exhibits at least one of the following conditions, namely an inlet temperature of about 250–400° C., an outlet temperature of about 50–75° C. and a residence time of the culture adjusted so as to obtain at least 10% survival after drying.

Other parameters may also influence the survival of the microorganisms. Thus, the relative humidity of the air at the outlet of the drying device may be of the order of about 10–40%, preferably 20–40%. Furthermore, it is possible to introduce into the composition which contains the microorganisms, before the spraying nozzle, an inert gas which may be used in food processes, especially $CO_2$, nitrogen, argon, helium, alone or in the form of a mixture.

If the culture of microorganisms alone is dried, the present process may thus provide a powder of microorganisms having a density of about 200–1000 g/l, but preferably 500–800 g/l, and having an Aw at 25° C. of about 0.05–0.5, with at least $10^7$ cfu/g but preferably $10^8$–$10^{11}$ cfu/g, and exhibiting a survival of the microorganisms of at least 10% per year when stored at 4–27° C., preferably of at least 90% per year. This powder of microorganisms may be preserved at refrigeration or freezing temperatures, before being used as inoculum for the fermentation of food, cosmetic or pharmaceutical products. This powder may also be administered directly by the oral route, or mixed with certain solid or liquid foods. It may be mixed with the milk used to fill an infant's feeding bottle, or it may even be mixed with milk powder. It may also be mixed with other foods intended to be administered by the enteral route to a hospitalized patient.

Likewise, if a dehydrated food composition is prepared, the present process may thus provide an easily dispersible food powder having a density of the order of about 200–1000 g/l, having an Aw at 25° C. of the order of about 0.05–0.5, having $10^9$ cfu/g, and exhibiting a survival of the microorganisms of at least 10% per year when stored at 20° C.

EXAMPLES

The present invention is described in greater detail below with the aid of the following examples of drying of cultures of lactic acid bacteria and of yeasts. The percentages are given by weight unless otherwise stated. It goes without saying, however, that these examples are given by way of illustration of the invention and do not constitute in any manner a limitation thereto.

Examples 1–4

A culture of the strain Lactobacillus johnsonii CNCM I-1225 of human origin, described in EP577904 (Société des Produits Nestlé) as being a probiotic strain which survives with difficulty in an oxygenated medium, is spray-dried.

For that, 3% of a fresh preculture, in an MRS medium, of the CNCM I-1225 strain is mixed with sterile MSK medium comprising powdered skimmed milk reconstituted at 10%, 0.1% commercial yeast extract, 0.5% peptone and 0.1% Tween 80, then it is fermented for 8 hours at 40° C., without stirring.

A large-scale culture of this strain is then prepared by fermenting a sterile MSK medium comprising powdered skimmed milk reconstituted at 10–25%, 0.1% commercial yeast extract, 0.5% peptone and 0.1% Tween 80, with 3% of the fermented mixture above, at 40° C., until a pH of 5.5 (about 1–3 hours) is obtained, with stirring at 30 revolutions per min and under a $CO_2$ atmosphere. The fermentation is continued at pH 5.5 by adding an alkaline base for a few hours. Then the culture is cooled to 15–20° C.

In Examples 1 to 4, 2% by weight of ascorbic acid and 1.25% by weight of sodium glutamate are added to the culture. Next, the various mixtures are spray-dried in a device adapted from that described in FIG. 1.c of U.S. Pat. No. 3,065,076, the only difference being that no agglomerating device is used, the powder which went into the dust recuperator associated with the dryer is recycled into the chamber, additional air having a temperature of 18–30° C. (depending on the ambient temperature) is injected near the heated air inlet simply by opening the chamber to the external medium; $CO_2$ and/or nitrogen is injected into the culture just before spraying.

It should further be noted that the powder is recovered on a fluidized bed passing through three compartments, the first two compartments serving to dry powder still further at temperatures of 60–90° C., and the last compartment serving to cool the powder to about 30° C. The operating conditions are described in Table 1 below.

After drying, the powder is recovered, part of it is diluted in sterile water and some of it is spread on an agar-MRS medium (De Man et al., 1960) in order to determine the number of surviving bacteria thereon.

The water activity of the powder, defined by the ratio of the partial vapor pressure of water at the surface of the powder to the vapour pressure of pure water at the same temperature is determined. The Aw can be determined by measuring the equilibrium relative humidity reached in a closed chamber at constant temperature. For that, a sample of a few g of powder is enclosed in a sealed container placed in a thermostated chamber at 25° C. The empty space around this sample reaches, at equilibrium, after 30–60 min, the same Aw value as the sample. An electronic sensor, mounted on the lid closing the container, then measures the humidity of this empty space by means of an electrolytic resistance.

The various powders of microorganisms are packaged in sealed containers comprising a nitrogen and/or $CO_2$ atmosphere, each container is preserved at 20° C. or 27° C. for 12 months, the number of surviving bacteria is determined periodically, then the number of months (value D) theoretically necessary to lose 90% of the lactic acid bacteria at 20° C. or 27° C. is calculated.

For comparison, under identical storage conditions the survival of batches of traditionally freeze-dried CNCM I-1225 bacteria is measured (by Hansen, D. K.), and the number of months (value D) theoretically necessary to lose 90% of the lactic acid bacteria at 20° C. or 27° C. is calculated.

TABLE 1

| Operating conditions | Example 1 | Example 2 | Example 3 | Example 4 |
|---|---|---|---|---|
| % dry matter | 27.31 | 13.13 | 27.89 | 26.75 |
| pH | 6.12 | 5.8 | 5.83 | 6.80 |
| Gas (l/min) | 5.6 ($CO_2$) | 2.2 ($N_2$) | 3.8 ($CO_2$) | 6.4 ($N_2/CO_2$) |
| Spraying pressure (bar) | 65 | 230 | 78 | 201 |
| Air at the inlet (° C.) | 317 | 310 | 320 | 309 |
| Hot air pressure (mbar) | 160 | 130 | 160 | 130 |
| Air at the outlet (° C.) | 64 | 60 | 71 | 72 |
| Humidity of the air at the outlet (%) | 21 | 20 | 21 | 28 |
| Humidity of the powder | 2.88 | 3.19 | 3.90 | 3.71 |
| Water activity of the powder (Aw) | 0.182 | 0.071 | 0.147 | 0.143 |
| Powder yield (kg/h) | 67 | 37 | 72 | 123 |
| Density of the powder (g/l) | 520 | 400 | 500 | 310 |
| Cfu/ml before spraying | $5.2 \times 10^8$ | $8 \times 10^8$ | $5.8 \times 10^8$ | $5.9 \times 10^8$ |
| Cfu/g after spraying | $2.2 \times 10^8$ | $9.65 \times 10^8$ | $2.7 \times 10^8$ | $3.2 \times 10^8$ |
| Loss of viability (log cfu/g) | 0.92 | 0.79 | 0.87 | 0.82 |
| Viability after drying (%) | 12.02 | 16.21 | 13.48 | 15.14 |
| Value D (months) at 20° C. | >12 | >12 | >12 | >12 |
| Value D (months) at 27° C. | >12 | >12 | >12 | >12 |

Value D for a batch of freeze-dried bacterium CNCM I-1225 preserved at 20° C.: 10.1 months
Value D for a batch of freeze-dried bacterium CNCM I-1225 preserved at 27° C.: 6.6 months The results presented in Table 1 above show that it is possible to obtain more than 16% survival of the lactic acid bacteria directly after drying, and a remarkable stability of the lactic acid bacteria after storage at high temperatures.

Example 5

A culture of the strain *Saccharomyces cerevisae* NCIMB 40612 described in EP663441 (Nestlé) is spray-dried.

For that, fermentation of the NCIMB 40612 strain is carried out according to the traditional fed-batch process by incubating at 30° C. with stirring (250 to 450 rpm) and increasing aeration (0.02 to 0.8 $m^3/h$), for 24 hours, maintaining the pH at 4.5 by adding suitable quantities of $NH_4OH$, controlling the foam produced by adding increasing quantities of antifoaming agent Contraspum 210 (1.5% by weight/volume of medium; Binggeli-Chemie, Switzerland), and regularly adding a suitable increasing quantity of "molasses" medium (84.85% sterile molasses, 13.85% water, 1% $H_2SO_4$).

The yeasts are then dried under the same conditions as those described in Example 2.

Example 6

This example is intended to show that the spraying of a food composition comprising less than 25% by weight of a culture of probiotic lactic acid bacteria may give less satisfactory survivals compared to those obtained with Examples 7 to 9 when a culture of probiotic bacteria and a food composition are co-sprayed.

A fermented milk is prepared as described in Examples 1 to 4, 2% by weight of ascorbic acid, 1.25% by weight of sodium glutamate and 300% by weight of concentrated milk having 50% by weight of dry matter are added thereto, then the mixture is spray-dried with the device described in Examples 1–4, and under the operating conditions described in Table 2 below. As described in Examples 1 to 4, after drying, the number of surviving bacteria is determined. The results are presented in Table 2 below.

Examples 7–9

Milk and a culture of the strain *Lactobacillus johnsonii* CNCM I-1225 are spray-dried together.

For that, a bacterial culture is prepared as described in Examples 1 to 4, protective agents are added thereto and 1 part of this culture of bacteria is continuously co-sprayed with about 40 to 100 parts of concentrated milk having 50% dry matter, the said sprayings being carried out together in devices adapted from that described in FIG. 1.c of U.S. Pat. No. 3,065,076.

As described in Examples 1 to 4, after spraying, the powder is recovered on a fluidized bed passing through 3 compartments, the first two compartments serving to dry the powder still further, at temperatures of 60–90° C., and the last compartment serving to cool the powder to about 30° C. The number of surviving bacteria in the dehydrated food powder is then determined, taking into account the dilution produced with the milk.

The results are presented in Table 2 below. The various powders exhibit, in addition, stabilities over time which are similar to those obtained with the powders of microorganisms described in Examples 1 to 4.

In Example 7, two sprayings are performed together in the device represented in FIG. 1.c of U.S. Pat. No. 3,065,076, the only difference being that no agglomerating device is used. The powder which went into the dust recuperator is recycled into the chamber. The additional air having a temperature of 18–30° C. (depending on the ambient temperature) is injected close to the heated air inlet simply by opening the chamber to the external medium. $CO_2$ is injected into the culture medium just before spraying. The culture and the milk are sprayed together with the aid of two nozzles whose ends are placed, in the chamber, at the level of the heated air inlet (same position as the nozzle 14 of FIG. 1.*c* of U.S. Pat. No. 3,065,076). The operating conditions are described in Table 2 below.

In Examples 8–9, the two sprayings are performed together in the device represented in FIG. 1.*c* of U.S. Pat. No. 3,065,076, the only difference being that no agglomerating device is used; the powder which went into the dust recuperator is recycled into the chamber, the recycled powder inlet halfway up the chamber; additional air having a temperature of 18–30° C. (depending on the ambient temperature) is injected close to the heated air inlet simply by opening the chamber to the external medium, and the milk is sprayed with the aid of a nozzle whose end is placed, in the chamber, at the level of the axis and the end of the heated air inlet (same position as the nozzle 14 of FIG. 1.*c* of U.S. Pat. No. 3,065,076). The bacterial culture is sprayed simultaneously with the aid of a nozzle whose end is placed, in the chamber, at the level of the axis and the end of the recycled powder inlet. The operating conditions are described in Table 2 below.

TABLE 2

| Operating conditions | Example 6 | Example 7 | Example 8 | Example 9 |
|---|---|---|---|---|
| Culture of bacteria | | | | |
| Protective agents | *Milk + A + SG | *M + A + T | *M + A + SG | *M + A + T |
| % dry matter | 41.82 | 31.08 | 28.79 | 31.08 |
| pH | 6.3 | 6.15 | 6.48 | 6.15 |
| Gas (l/min) | 6.5 ($CO_2$) | 2.5 ($CO_2$) | — | — |
| Flow rate (l/h) | 496.3 | 78 | 30 | 53 |
| Spraying pressure (bar) | 59 | 70 | 8 (nozzles with two phases: $N_2$) | 8 (nozzles with two phases: $N_2$) |
| Milk | | | | |
| % dry matter | — | 46.88 | 46.88 | 46.88 |
| Flow rate (kg/h) | — | 378 | 556 | 420 |
| Spraying pressure (bar) | — | 30 | 48 | 38 |
| Air at the inlet (°C.) | 310 | 309 | 310 | 305 |

TABLE 2-continued

| Operating conditions | Example 6 | Example 7 | Example 8 | Example 9 |
|---|---|---|---|---|
| Pressure of the hot air (mbar) | 190 | 164 | 190 | 160 |
| Air at the outlet (° C.) | 65 | 65 | 64 | 65 |
| Humidity of the air at the outlet (%) | 20.7 | 20 | 24.2 | 20.6 |
| Humidity of the powder (%) | 3.3 | 3.5 | 3.8 | 4.0 |
| Powder yield (kg/h) | 215 | 209 | 280 | 220 |
| Density of the powder (g/l) | 440 | 535 | 335 | 320 |
| Cfu/ml before spraying | 1.2 × 10 | $4.45 \times 10^9$ | $9.63 \times 10^9$ | $5.81 \times 10^9$ |
| Cfu/g after spraying | $5.3 \times 10^6$ | $6 \times 10^7$ | $6.5 \times 10^7$ | $8.2 \times 10^7$ |
| Loss of viability (log cfu/g) | 3.72 | 1.42 | 1.19 | 1.23 |
| Viability after drying (%) | <0.1 | 3.8 | 6.45 | 5.89 |

*Milk + A + SG: 300% concentrated milk having 50% dry matter + 2% ascorbic acid + 1.25% sodium glutamate
*M + A + SG: 100% concentrated milk having 50% dry matter + 2% ascorbic acid + 1.25% sodium glutamate
*M + A + T: 100% concentrated milk having 50% dry matter + 5% ascorbic acid + 1.25% sodium glutamate

Example 10

A culture of lactic acid bacteria CNCM I-1225 comprising 5% ascorbic acid and 5% trehalose, and finely divided concentrated tomato juice having 50% dry matter are sprayed together under the conditions described in Example 8.

Example 11

A culture of lactic acid bacteria CNCM I-1225 comprising 5% ascorbic acid and 5% trehalose, and a soya-based vegetable milk having 50% dry matter are sprayed together under the conditions described in Example 8.

We claim:

1. Spray-drying process in which a composition comprising water and microorganisms for use as a food additive is prepared as a powder by spraying the composition in a spray-drying device having a heated air inlet temperature of about 250–400° C. and an air outlet temperature of about 50–75° C. to provide a dry powder, with the composition being present in the device for a residence time that is controlled or adjusted so as to obtain survival of at least 10% of the microorganisms after drying.

2. Process according to claim 1 which further comprises concentrating the composition before spraying.

3. Process according to claim 2, which further comprises concentrating the composition to less than 70% water.

4. Process according to claim 1, which further comprises controlling the residence time of the composition in the drying device so as to obtain a powder having an Aw at 25° C. of between about 0.05 and 0.5.

5. Process according to claim 1, which further comprises including in the composition at least one protective agent selected from the group consisting of vitamins, amino acids, proteins or protein hydrolysates obtained from milk or soya, sugar, and fats.

6. Process according to claim 1, which further comprises including in the composition at least 80% by dry weight of a food composition before spraying.

7. Process according to claim 1, wherein the composition includes a mixture of the microorganisms and a food composition and the mixture is sprayed by the spray drying device.

8. Process according to claim 7, wherein the composition contains 1 part of a culture of microorganisms and at least 1 part of the food composition in the mixture, the said parts being calculated in the dry state.

9. A process for providing a dry microorganism-containing composition, which comprises:

forming a composition which contains water and a number of microorganisms for use as a food additive;

spraying the composition in a spray-drying device wherein the composition is heated to a temperature of about 250 to 400° C. and retained in the spray-drying device for a residence time sufficient to remove water from and dry the composition;

cooling the heated, dried composition to about 50 to 75° C. to provide a dry powder; and controlling the residence time in the spray-drying device to obtain survival of at least 10% of the initial number of microorganisms.

10. Process according to claim 9, which further comprises concentrating the composition before spraying.

11. Process according to claim 10, which further comprises concentrating the composition to less than 70% water.

12. Process according to claim 9, which further comprises controlling the residence time of the composition in the drying device so as to obtain a powder having an Aw at 25° C. of between about 0.05 and 0.5.

13. Process according to claim 9, which further comprises including in the composition at least one protective agent selected from the group consisting of vitamins, amino acids, proteins or protein hydrolysates obtained from milk or soya, sugars, and fats.

14. Process according to claim 9, which further comprises including in the composition at least 80% by dry weight of a food composition before spraying.

* * * * *